(12) United States Patent
Watts

(10) Patent No.: US 11,857,236 B1
(45) Date of Patent: Jan. 2, 2024

(54) ORTHOPEDIC SCREW

(71) Applicant: RetroFix Screws, LLC, Salisbury, NC (US)

(72) Inventor: Hugh Boyd Watts, Salisbury, NC (US)

(73) Assignee: RETROFIX SCREWS, LLC, Salisbury, NC (US)

( * ) Notice: Subject to any disclaimer, the term of this patent is extended or adjusted under 35 U.S.C. 154(b) by 0 days.

(21) Appl. No.: 18/329,184

(22) Filed: Jun. 5, 2023

(51) Int. Cl.
| | |
|---|---|
| *A61B 17/68* | (2006.01) |
| *A61B 17/88* | (2006.01) |
| *A61B 17/86* | (2006.01) |
| *A61B 90/00* | (2016.01) |

(52) U.S. Cl.
CPC ...... *A61B 17/8685* (2013.01); *A61B 17/8625* (2013.01); *A61B 90/06* (2016.02); *A61B 2090/062* (2016.02)

(58) Field of Classification Search
CPC . A61B 17/8685; A61B 17/8625; A61B 90/06; A61B 2090/062
USPC ....... 606/53, 60, 65, 68, 301, 304, 305, 307, 606/308, 309, 310, 311, 312, 318, 323, 606/325, 328, 105
See application file for complete search history.

(56) References Cited

U.S. PATENT DOCUMENTS

| | | | |
|---|---|---|---|
| 9,044,843 B1 * | 6/2015 | Mokhtee | B25B 15/005 |
| 9,655,661 B1 | 5/2017 | Watts | |
| 10,729,478 B1 | 8/2020 | Watts | |
| 10,952,780 B1 | 3/2021 | Watts | |
| 2005/0107791 A1 | 5/2005 | Manderson | |
| 2013/0041414 A1 * | 2/2013 | Epperly | A61B 17/7266 606/310 |
| 2014/0277186 A1 | 9/2014 | Granberry et al. | |
| 2015/0359573 A1 | 12/2015 | Adams et al. | |
| 2016/0081727 A1 | 3/2016 | Munday et al. | |

(Continued)

FOREIGN PATENT DOCUMENTS

| | | | | |
|---|---|---|---|---|
| AU | 2010201014 A1 * | 10/2010 | | A61B 17/68 |
| EP | 3463105 A1 | 4/2019 | | |

(Continued)

OTHER PUBLICATIONS

European Search Report dated Nov. 26, 2020 prepared by the European Patent Office in Munich, Germany related to Application No. EP 20178053; Application No./Patent No. 20178053.3-1132. (References cited in report are provided).

*Primary Examiner* — Eduardo C Robert
*Assistant Examiner* — David C Comstock
(74) *Attorney, Agent, or Firm* — Shumaker, Loop & Kendrick, LLP; Lloyd J. Wilson

(57) ABSTRACT

Methods, devices, and kits include an orthopedic screw that is configured to be at least partially withdrawn from bone segment(s) and has, in part, a shaft extending from a distal end to a proximal end, screw threads with a first threaded alignment formed on the distal end, an unthreaded shank, a head positioned on the proximal end, and an enlarged terminal end segment of the head that includes (1) a socket for receiving a tool adapted for rotating the screw into the bone segment(s), and (2) a threaded cannula portion centrally located at a focus point of the enlarged terminal end and extending along a cannula for at least a portion of a length of the head comprising a second threaded alignment opposite the first threaded alignment and configured to receive an instrument head.

14 Claims, 19 Drawing Sheets

(56) References Cited

U.S. PATENT DOCUMENTS

2017/0058935 A1* 3/2017 Li .................. F16B 35/042
2018/0098838 A1* 4/2018 Hoof ............... A61B 17/8888

FOREIGN PATENT DOCUMENTS

| WO | 2009152270 A1 | 12/2009 |
| WO | 20170147537 A1 | 8/2017 |
| WO | 20170210574 A1 | 12/2017 |

* cited by examiner

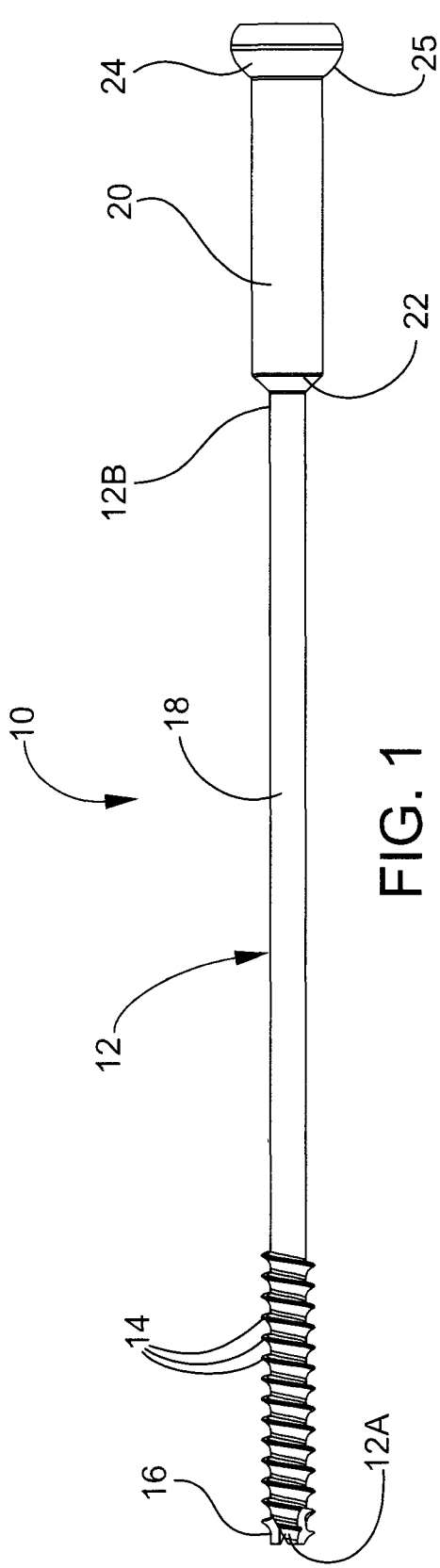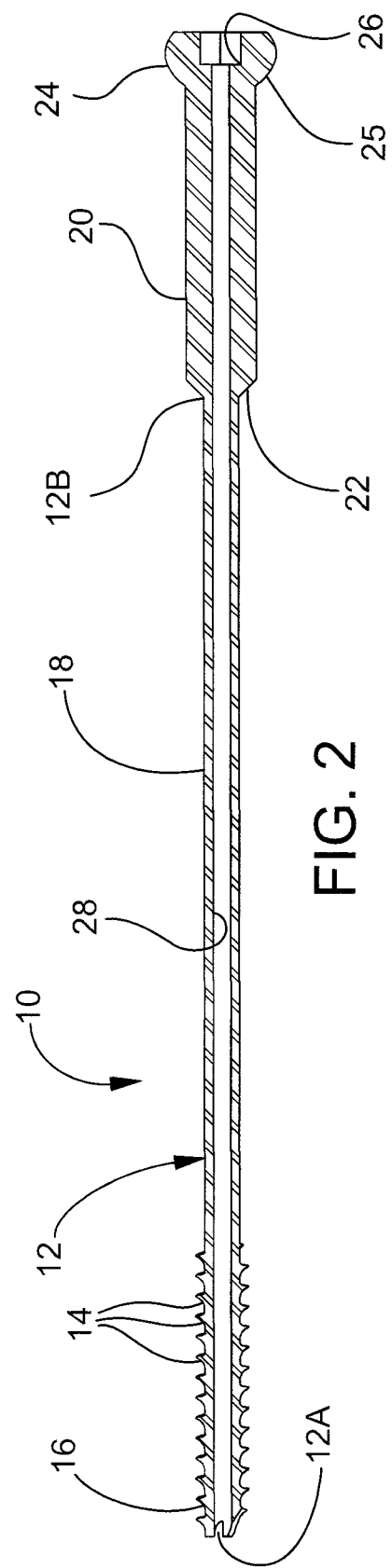

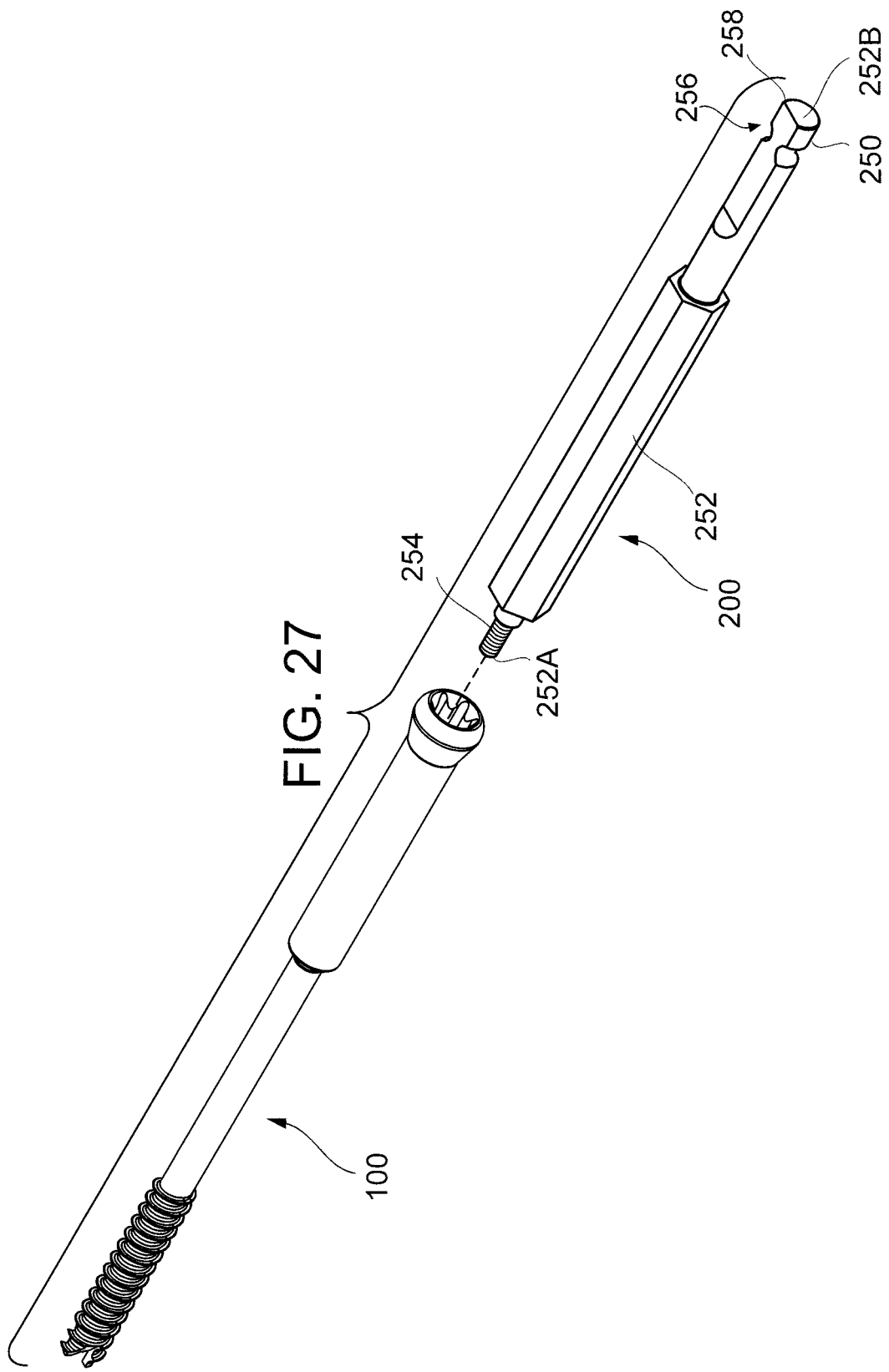

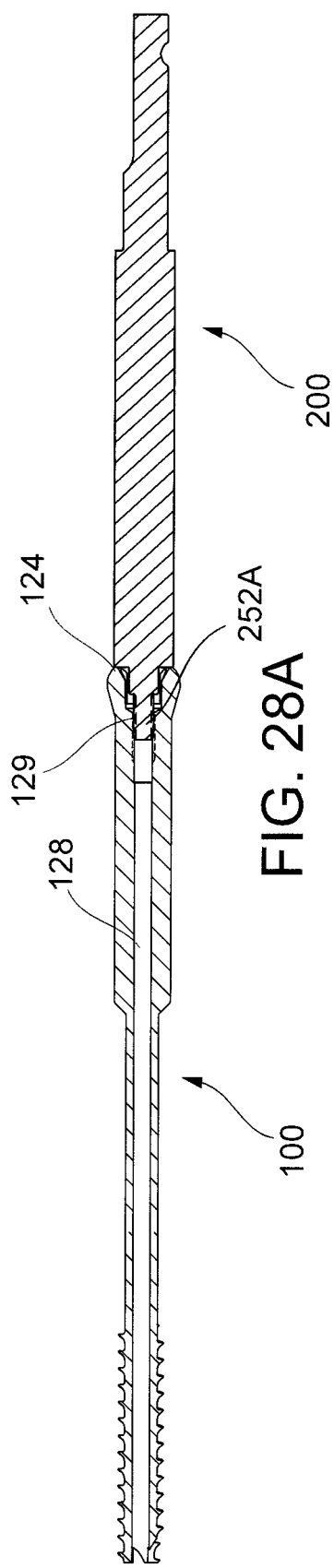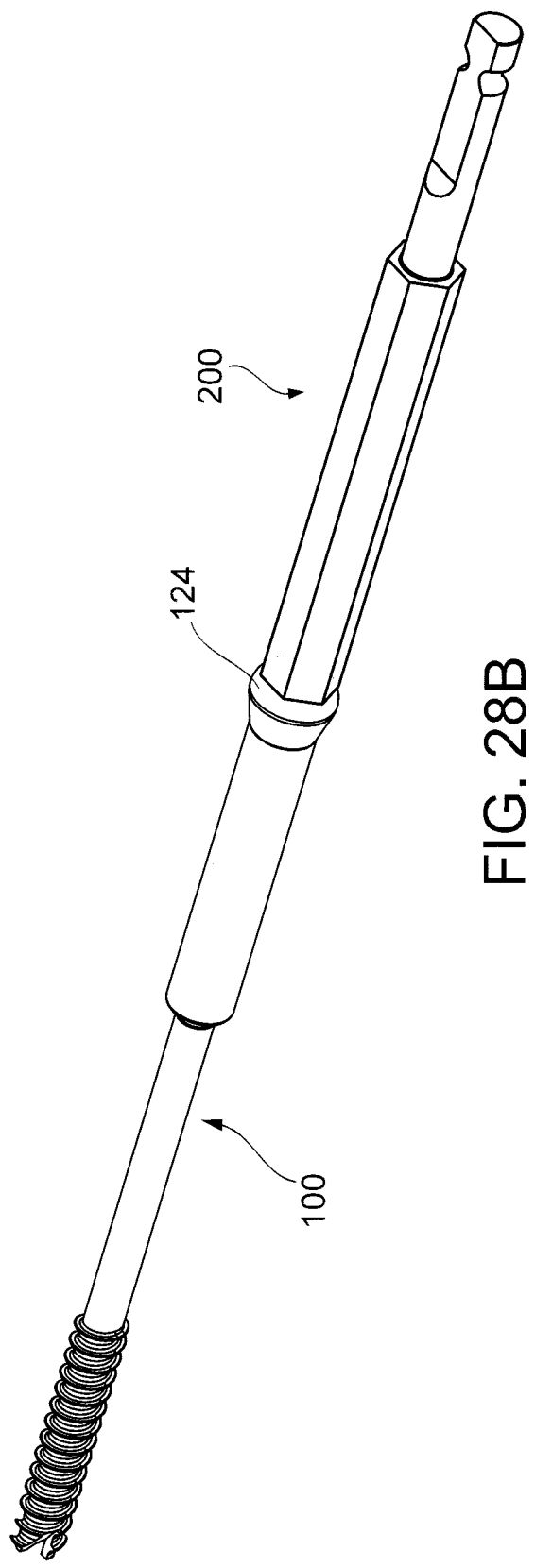

300

```
ACCESSING AN IMPLANTED ORTHOPEDIC SCREW PREVIOUSLY IMPLANTED IN ONE
OR MORE BONE SEGMENTS OF A PATIENT, THE ORTHOPEDIC SCREW, COMPRISING A
UNITARY SHAFT, INCLUDING:

(I)    SCREW THREADS COMPRISING A FIRST THREADED ALIGNMENT AND
    HAVING A DIAMETER AND FORMED ON A FIRST, DISTAL END OF THE SHAFT, A
    TERMINAL END PORTION OF THE SCREW THREADS INCLUDING AN END EDGE
    ADAPTED TO FACILITATE PASSAGE OF THE SCREW THROUGH THE ONE OR MORE
    BONE SEGMENTS AT A FRACTURE SITE;

(II)   AN UNTHREADED SHANK HAVING A DIAMETER LESS THAN THE
    DIAMETER OF THE SCREW THREADS;

(III)  A HEAD POSITIONED ON SECOND, PROXIMAL END OF THE SHAFT
    INTEGRALLY-FORMED TO THE SHANK AND HAVING A DIAMETER GREATER THAN
    THE DIAMETER OF THE SCREW THREADS AND THE SHANK;

(IV)   AN ENLARGED TERMINAL END SEGMENT OF THE HEAD INCLUDING:

(1)    A SOCKET FOR RECEIVING A TOOL ADAPTED FOR ROTATING THE
        SCREW INTO THE ONE OR MORE BONE SEGMENTS AT THE FRACTURE SITE;
        AND (2)    A THREADED CANNULA PORTION CENTRALLY LOCATED WITHIN
        THE SOCKET AT A FOCUS POINT OF THE ENLARGED TERMINAL END AND
        EXTENDING ALONG A CANNULA FOR AT LEAST A PORTION OF A LENGTH OF
        THE HEAD, THE THREADED CANNULA PORTION COMPRISING A SECOND
        THREADED ALIGNMENT OPPOSITE THE FIRST THREADED ALIGNMENT OF THE
        SCREW THREADS AND CONFIGURED TO RECEIVE AN INSTRUMENT HEAD
        ADAPTED FOR ROTATING THE IMPLANTED ORTHOPEDIC SCREW FOR
        REMOVAL
```
— 305

```
FASTENING THE INSTRUMENT HEAD ADAPTED FOR ROTATING THE IMPLANTED
ORTHOPEDIC SCREW TO THE THREADED CANNULA PORTION OF THE ENLARGED
TERMINAL END
```
— 310

```
AT LEAST PARTIALLY WITHDRAWING THE IMPLANTED ORTHOPEDIC SCREW FROM THE
ONE OR MORE BONE SEGMENTS BY ROTATING THE INSTRUMENT HEAD
```
— 315

FIG. 30

ORTHOPEDIC SCREW

CROSS-REFERENCE TO RELATED APPLICATIONS

This application is related to U.S. Pat. No. 9,655,661 B1 entitled "Cannulated Orthopedic Screw and Method of Reducing and Fixing a Fracture of the Lateral Malleolus" filed on Jun. 30, 2016, U.S. Pat. No. 10,729,478 B1 entitled "Cannulated Orthopedic Screw and Method of Reducing a Fracture of the Lateral Malleolus" filed on Nov. 22, 2019, U.S. Pat. No. 10,952,780 B1 entitled "Method of Reducing a Fracture of the Lateral Malleolus" filed on Jun. 26, 2020, and International Patent Cooperation Treaty (PCT) Application No. PCT/US2021/038406 entitled "Method of Reducing a Fracture of the Lateral Malleolus" filed on Jun. 22, 2021, and the entire contents of each of which are hereby expressly incorporated herein by reference.

FIELD OF THE INVENTION

This invention relates generally to methods, devices and kits related to a cannulated orthopedic screw, and more particularly embodiments of the invention related to methods, devices, and kits related to removal of an implanted cannulated orthopedic screw.

BACKGROUND OF THE INVENTION

The ankle joint is made up of three bones coming together. The tibia, which is the main bone of the lower leg, makes up the medial, or inside, anklebone. The fibula is a smaller bone that parallels the tibia in the lower leg and makes up the lateral, or outside, anklebone. The enlarged distal ends of both the tibia and fibula are known as the malleoli (singular "malleolus"). Together, they form an arch that sits on top of the talus, one of the bones in the foot. These three bones (tibia, fibula, and talus) make up the bony elements of the ankle joint. A fibrous membrane called the joint capsule, lined with a smoother layer called the synovium, encases the joint architecture. The joint capsule contains the synovial fluid produced by the synovium. The synovial fluid allows for smooth movement of the joint surfaces. The ankle joint is stabilized by several ligaments, which hold these bones in place.

Ankle fractures occur when one or both of the malleoli are broken. These fractures are very common. Ankle fractures can happen after falls, car accidents or severe twisting of the ankle. One, two or all three malleoli can be broken. Fixation procedures for a lateral malleolus fracture have evolved over many years. Initial preferred treatment was a closed reduction of the fracture and immobilizing the malleolus with a cast or splint. Later practices have included the use of rush rods, screws and simple plates that join the fracture but without axial compression. More recent treatments have included the use of stronger and wider plates with screws or locking plates that still join the fracture but without axial compression.

Patients are instructed in non-weight bearing or minimal weight-bearing activities based on the fracture pattern, bone density, weight of the patient, mental condition and level of fixation obtained at surgery. Accurate and complete fixation in young patients is essential for good long-term results but even with accurate fixation, some patients develop non-union or articular cartilage damage and require some type of replacement later due to the cartilage damage or infection.

Older patients with osteopenia or age-related physical problems require a different approach. Most fixations of the lateral malleolus, if displaced, require open stripping of tissue from the distal fibula and plate fixation with multiple cortical and cancellous screws. A distal-to-proximal fixation of the lateral malleolus offers another way to reduce and stabilize the lateral malleolus. Such a procedure alleviates the need for open fixation, i.e., an incision and tissue retraction along the length of the ankle through which plates are mounted to the side of the bones with laterally-inserted screws. Lateral fixation with plates and screws is particularly problematic in older patients with Alzheimer's, osteoporosis, and other medical conditions. A distal-to-proximal fixation of the lateral malleolus permits a quicker fixation with a retrograde screw from the distal tip of the lateral malleolus up the medullary canal of the proximal fibula. Applicant's U.S. Pat. No. 9,655,661 discloses one advancement in lateral malleolus fixation utilizing a screw that includes screw threads along the entire length of the shaft of the screw.

The present application discloses a further improvement in with a screw that has enhanced features that facilitate implant removal.

SUMMARY OF THE INVENTION

Shortcomings of the prior art are overcome and additional advantages are provided through the provision of a method that comprises the steps of: (a) accessing an implanted orthopedic screw previously implanted in one or more bone segments of a patient, the orthopedic screw, comprising a unitary shaft, including: (i) screw threads comprising a first threaded alignment and having a diameter and formed on a first, distal end of the shaft, a terminal end portion of the screw threads including an end edge adapted to facilitate passage of the screw through the one or more bone segments at a fracture site; (ii) an unthreaded shank having a diameter less than the diameter of the screw threads; (iii) a head positioned on second, proximal end of the shaft integrally-formed to the shank and having a diameter greater than the diameter of the screw threads and the shank; (iv) an enlarged terminal end segment of the head including: (1) a socket for receiving a tool adapted for rotating the screw into the one or more bone segments at the fracture site; and (2) a threaded cannula portion centrally located within the socket at a focus point of the enlarged terminal end and extending along a cannula for at least a portion of a length of the head, the threaded cannula portion comprising a second threaded alignment opposite the first threaded alignment of the screw threads and configured to receive an instrument head adapted for rotating the implanted orthopedic screw for removal; and (b) fastening the instrument head adapted for rotating the implanted orthopedic screw to the threaded cannula portion of the enlarged terminal end; (c) at least partially withdrawing the implanted orthopedic screw from the one or more bone segments by rotating the instrument head.

Also disclosed herein is an implant device comprising an orthopedic screw comprising: (i) a unitary shaft extending from a first, distal end to a second, proximal end; (ii) screw threads comprising a first threaded alignment and having a diameter and formed on the first, distal end, a terminal end portion of the screw threads including an end edge adapted to facilitate passage of the screw through the one or more bone segments at a fracture site; (iii) an unthreaded shank having a diameter less than the diameter of the screw threads; (iv) a head positioned on the second, proximal end integrally-formed to the shank and having a diameter greater than the diameter of the screw threads and the shank; and (v) an enlarged terminal end segment of the head including: (1) a socket for receiving a tool adapted for rotating the screw into one or more bone segments at the fracture site; and (2) a threaded cannula portion centrally located at a focus point of the enlarged terminal end and extending along a cannula for at least a portion of a length of the head, the threaded cannula portion comprising a second threaded alignment opposite the first threaded alignment of the screw threads and configured to receive an instrument head adapted for rotating the implanted orthopedic screw for removal.

Also disclosed herein is a surgical kit comprising: (A) an orthopedic screw comprising: (i) a unitary shaft extending from a first, distal end to a second, proximal end; (ii) screw threads comprising a first threaded alignment and having a diameter and formed on the first, distal end, a terminal end portion of the screw threads including an end edge adapted to facilitate passage of the screw through one or more bone segments at a fracture site; (iii) an unthreaded shank having a diameter less than the diameter of the screw threads; (iv) a head positioned on second, proximal end integrally-formed to the shank and having a diameter greater than the diameter of the screw threads and the shank; and (v) an enlarged terminal end segment of the head including: (1) a socket for receiving a tool adapted for rotating the screw into the one or more bone segments at the fracture site; and (2) a threaded cannula portion centrally located at a focus point of the enlarged terminal end and extending along a cannula for at least a portion of a length of the head, the threaded cannula portion comprising a second threaded alignment opposite the first threaded alignment of the screw threads and configured to receive an instrument head; and (B) the instrument head adapted for rotating the implanted orthopedic screw for removal.

BRIEF DESCRIPTION OF THE DRAWING FIGURES

The present invention is best understood when the following detailed description of the invention is read with reference to the accompanying drawings, in which:

FIG. 1 is a side longitudinal elevation of an orthopedic screw in accordance with one preferred embodiment of the invention;

FIG. 2 is a side vertical cross-section of an orthopedic screw in accordance with one preferred embodiment of the invention;

FIGS. 12-25 illustrate the detailed sequence of method steps for carrying out the surgical technique involved in inserting the cannulated screw;

FIG. 27 illustrates a perspective view of a kit that includes the implant of FIGS. 26A-26C and an instrument for implant removal, according to one embodiment;

FIG. 28A illustrates a cross sectional view of the implant of FIGS. 26A-27 with the instrument for implant removal of FIG. 27 inserted therein, according to one embodiment;

FIG. 28B illustrates a perspective view of the implant and instrument for implant removal of FIGS. 26A-28A, according to one embodiment;

FIG. 30 illustrates example method steps for removing an implant, according to one embodiment.

DETAILED DESCRIPTION

Figure 3:
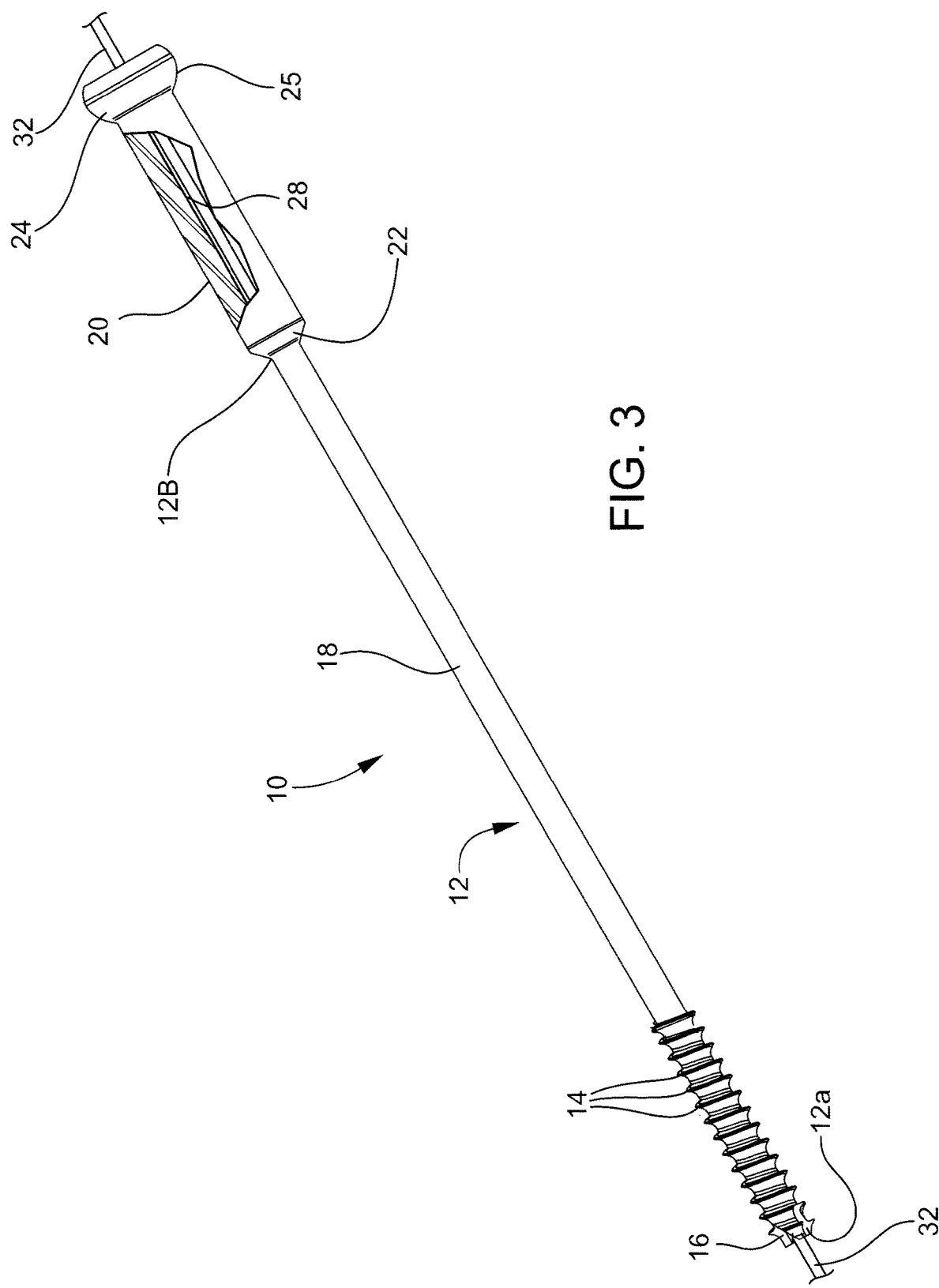
FIG. 3 is a side partial vertical cross-section of an orthopedic screw in accordance with one preferred embodiment of the invention showing a K-wire extending through the cannula of the screw.
Figure 4:
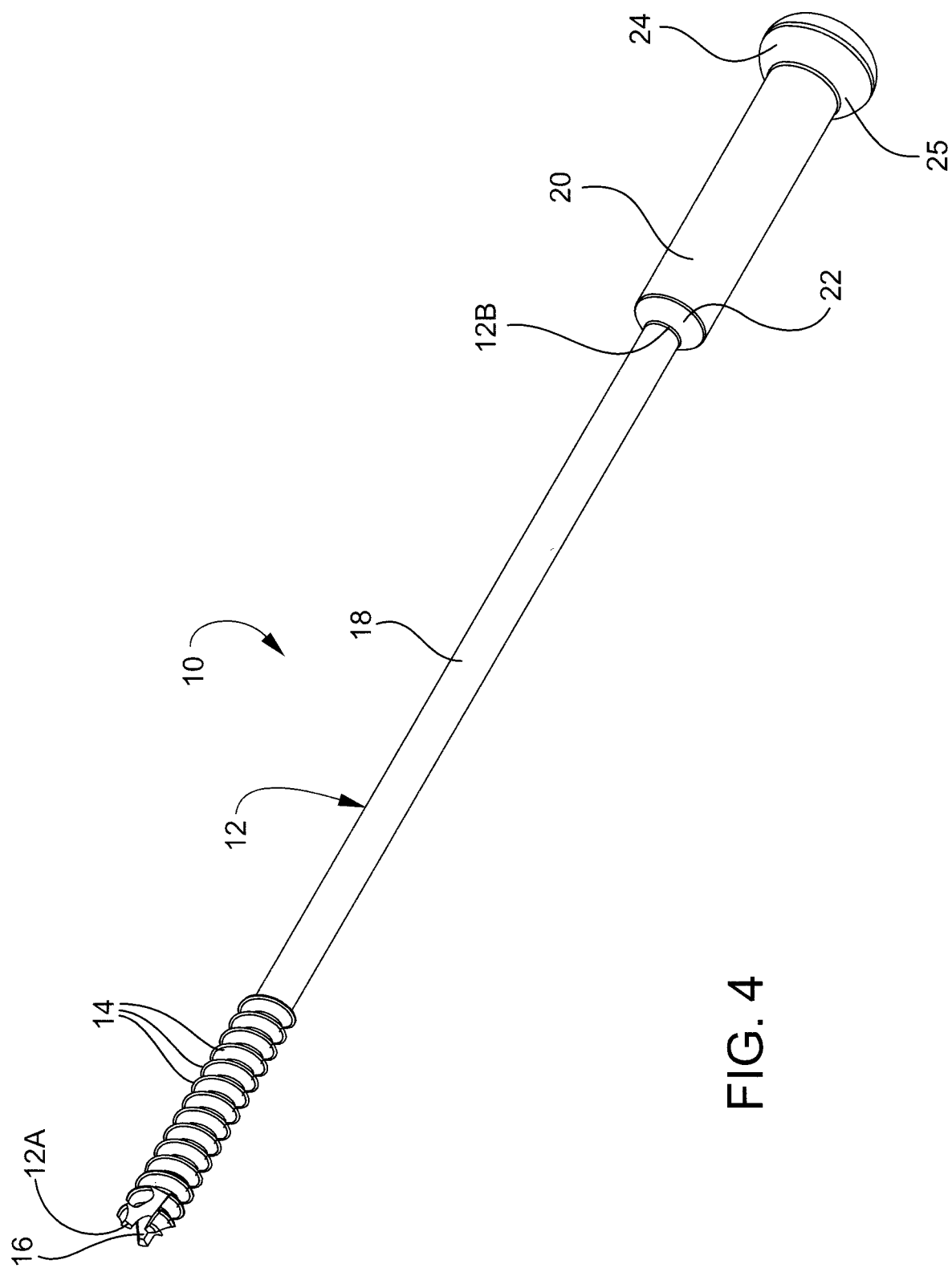
FIG. 4 is a perspective view of the screw as viewed from the threaded end of the screw.

Referring now to the drawings, an orthopedic screw used in practicing the method of the invention is shown at reference numeral 10 in the drawing Figures. Referring specifically to FIGS. 1-4, the screw 10 is fabricated of, for example, surgical grade steel, titanium, alloys thereof or other suitable materials, including suitable medical-grade coatings and/or finishes. Screw 10 includes a unitary shaft 12 with screw threads 14 formed on the shaft 12 proximate a distal first end 12A of the shaft 12. The screw threads 14 terminate at a sharp, biting end edge 16 adapted to facilitate passage of the screw 10 axially through a lateral malleolus "M" and fibula "F" (see FIGS. 8 and 9) at a fracture site.

Actual threads are 5.7 threads/cm for an HA 4.5 Screw and 6.7 threads/cm for an HA 4.0 Screw. Medical screw threads are defined as HA or HB. According to a preferred embodiment an HA 4.0 or an HA 4.5 screw thread is used, and are preferably "modified buttress threads." The modified buttress thread is used to increase compression and prevent easy pullout of the screw 10.

An unthreaded shank 18 of the shaft 12 extends to a proximate second end 12B of the shaft 12 and has a diameter less than the major diameter of the screw threads 14. A head 20 is formed on the second end 12B of the shaft 12 with a first tapered transition segment 22 formed at the juncture of the shaft 12 and an elongate enlarged head 20 such that rotation of the screw 10 provides progressively increased fracture-reducing pressure between the fibula and malleolus bone fragments as the first tapered transition segment 22 drives the malleolus against the fibula, as described in further detail below. The head 20 has a predetermined large diameter in relation to the diameter of the shaft 12.

The length of the screw threads 14 in relation to the overall length of the screw 10 is preferably approximately 19 to 31 percent. For example, for a screw 10 with a screw thread 14 length of 25 mm and a total shaft length of 130 mm, the screw threads 14 represent approximately 19 percent (25 mm/130 mm) of the total screw 10 length. For a screw 10 with a screw thread 14 length of 25 mm and a total shaft length of 80 mm, the screw threads 14 represent approximately 31 percent (25 mm/80 mm) of the total screw 10 length.

A further enlarged proximal end 24 of the head 20 includes an axially-aligned socket 26 adapted for receiving a tool, for example a hex or star tool, and for rotating the screw 10 into aligned fibula and malleolus bone fragments at the fracture site. The head 20 transitions to the proximal end 24 of the head by a second tapered transition segment 25. Rotation of the screw 10 provides progressively increased fracture-reducing pressure between the fibula and malleolus bone fragments as the second tapered transition segment 25 drives the malleolus against the fibula. Thus, both the first tapered transition segment 22 and the second tapered transition segment 25 collectively apply pressure as the screw 10 is driven into its required fixation position. This screw design provides three distinct spaced-apart points of compression along the length of the screw 10 that are capable of applying pressure required to reduce the fracture in a therapeutically appropriate manner. In situations where the fracture has a significant axial component that extends along a portion of both the malleolus and the fibula, the second tapered transition segment 25 insures that there will be pressure applied by the interaction with the screw threads 14.

A cannula 28 extends through the screw 10 from the socket 26 to the first end 12A of the shaft 12 so that a Kirschner wire, known as a "K-wire" or "surgical wire" can be passed completely through the screw 10 to act as a guide when driving the screw 10 into the aligned fibula and malleolus bone fragments.

Figure 5:
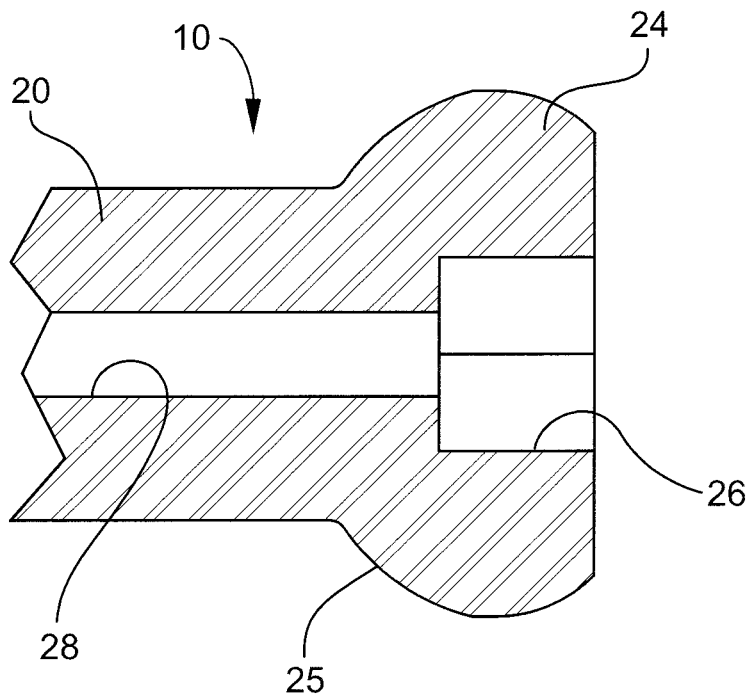
FIG. 5 is a vertical cross-section of the enlarged terminal end of the head of the screw within which the socket is located.
Figure 6:
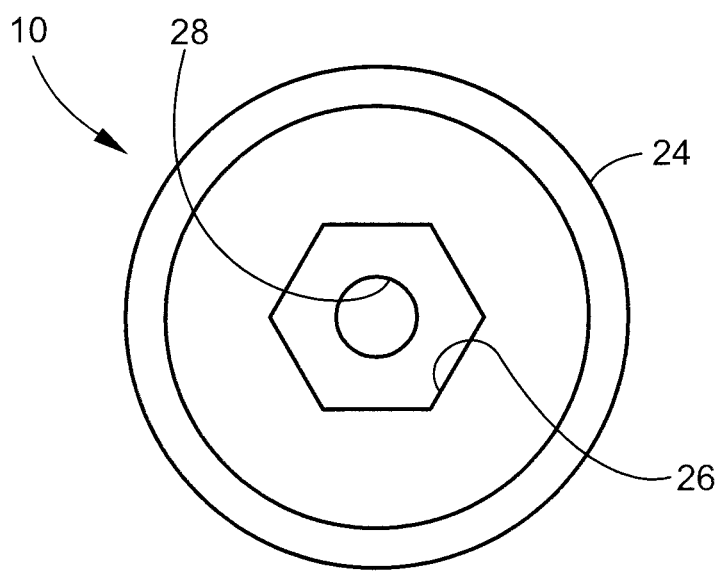
FIG. 6 is a lateral cross-section of the enlarged terminal end of the head of the screw within which the socket is located, showing a hex-configured socket.

FIGS. 5 and 6 show details of the socket 26 and the head 20.

Figure 7:
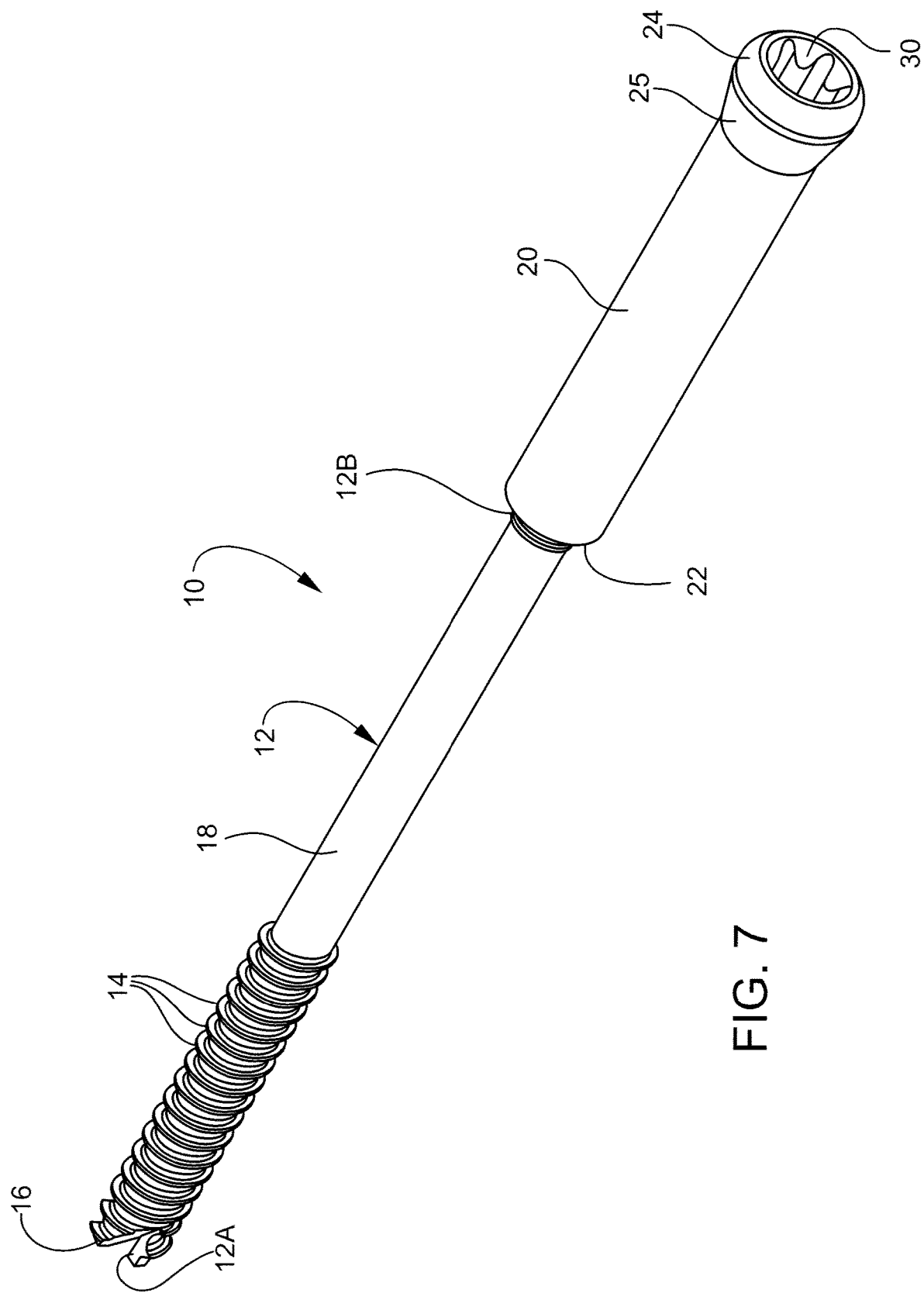
FIG. 7 is a perspective view of the screw as viewed from the head end of the screw and showing a star bit-configured socket.

FIG. 7 shows a version of the screw 10 with a socket 30 known as a "star" socket that has a 6-point star-shaped pattern that is rotated with a star bit, also referred to by its registered trademark "Torx."

Figure 8:
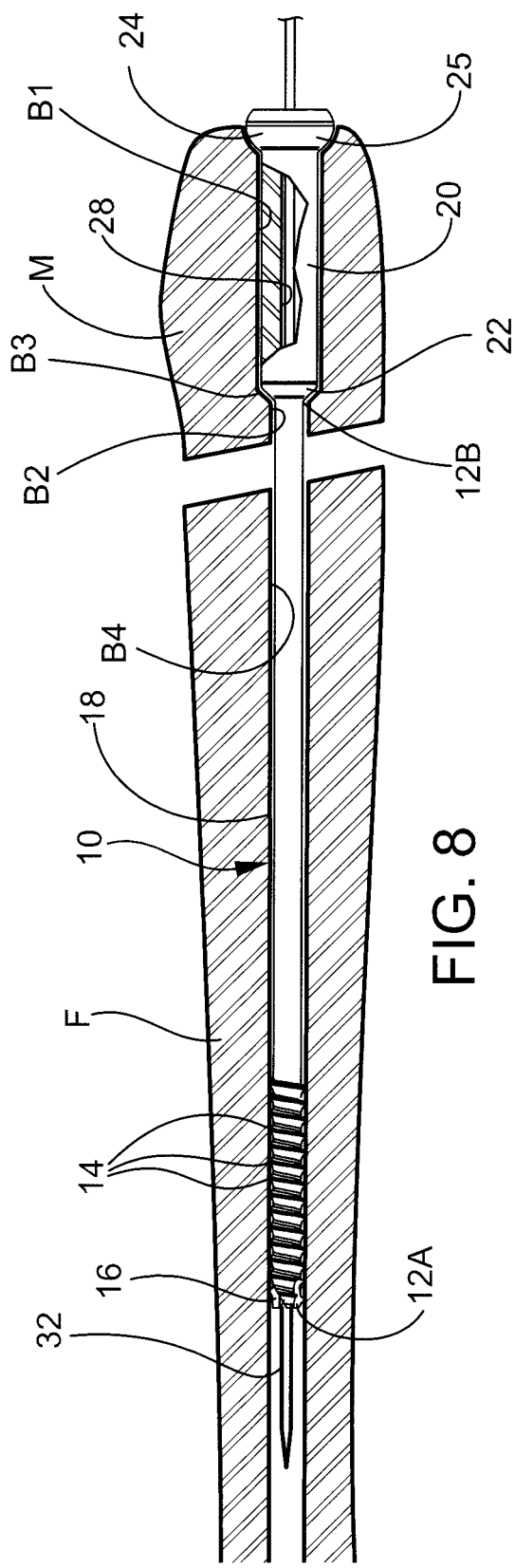
FIG. 8 is a partial vertical schematic cross-section showing the position of the screw before reduction of the fracture has occurred.
Figure 9:
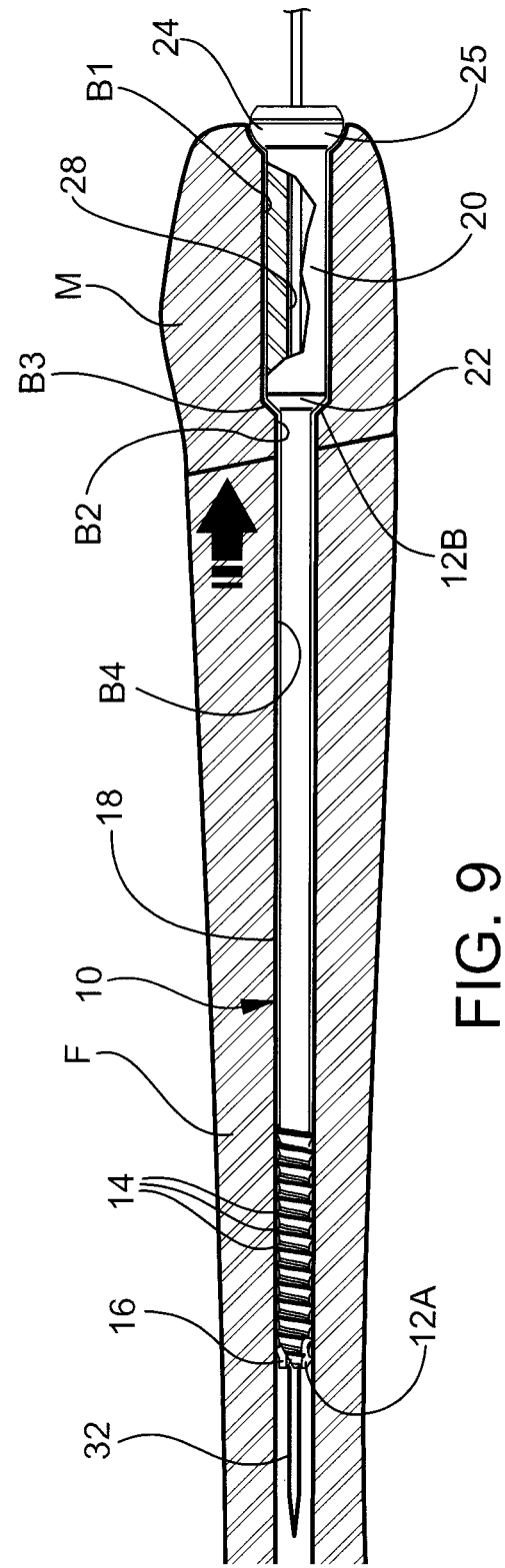
FIG. 9 is a partial vertical schematic cross-section showing the position of the screw after reduction of the fracture has occurred.

Referring now to FIGS. 8 and 9, to reduce a fracture a bore is formed in the lateral malleolus "M" and the medullary canal of the fibula "F." As shown schematically, the bore in the malleolus includes a distal large diameter segment B1 and a proximal small diameter segment B2 communicating with the large diameter segment B1 and defines a radially-inwardly extending shoulder B3. The bore in the medullary canal of the fibula F is shown at B4.

To reduce the fracture, an incision is made in the ankle to expose a distal end of a lateral malleolus. A drill guide is placed into the incision abutting the exposed distal end of the lateral malleolus. A bit having a cannula therethrough is amounted into a driver and the bit is then inserted into the drill guide in proximity to the exposed lateral malleolus. The bit is driven into and through the lateral malleolus M and into a position proximate to and aligned with the medullary canal of the fibula F forming a bore B1-B4.

A surgical wire 32 is inserted into the cannula of the bit while the bit is still positioned in the just-formed bore B1-B4 in the lateral malleolus M and the medullary canal of the fibula F. The bit is then withdrawn, leaving the surgical wire 32 in the bore B1-B4 to act as a guide for the screw 10 when inserted.

A screw 10 is selected from a range of sizes, for example, an overall length of between 80 mm to 130 mm, a head 20 diameter of 5 mm to 6 mm and a head 20 length of between 20 mm and 40 mm. The screw 10 is guided on the wire 32 into the bore B1-B4 of the fracture site.

The screw 10 is rotated into a position where the lateral malleolus M and the fibula F are aligned in a fixed position in intimate contact and the fracture is thus reduced. The threads 14 of the screw 10 facilitate cortical purchase of the screw 10 within the medullary canal of the fibula F. The relatively long unthreaded shank 18 of the shaft 12 assists in preserving adequate thickness of the surrounding bone of the fibula F and distinguishes the screw 10 from prior art screws that include threads along the entire shaft of the screw.

By continuing to rotate the screw 10 until the tapered transition segment 22 of the screw 10 bears against the shoulder B3 of the bore in the malleolus M, the fibula F and the malleolus M are drawn together into a correctly aligned reduction position. Further rotation of the screw 10 drives the first tapered transition segment 22 of the screw into a compression state against the shoulder B3 of the malleolus M. This method step also provides enhanced reduction that will improve healing by increasing blood flow between the adjacent bones at the fracture site. After the screw 10 is in its final position, the wire 32 is removed by withdrawing it from the cannula 28 of the screw 10 through the socket 26.

The above-procedures are preferably carried out using, for example, a fluoroscopy x-ray apparatus that permits the physician or technician to view in real-time the positions of the bones, drill bit, screw 10 and surgical wire 32 relative to each other, and to determine an appropriate screw size by positioning a screw 10 over the fracture site and viewing the juxtaposition of the screw in relation to the fracture.

The screw can be manufactured in a range of sizes to facilitate use on patients of varying ages, gender and body size. A typical range of sizes is set out below:

| | |
|---|---|
| Total length of screw 10 | 80-130 mm |
| Length of head 20 | 20-40 mm |
| Length of threads 14 | 25 mm |
| Diameter of enlarged terminal end 24 of the head 20 | 6.5 mm |
| Diameter of head 20 | 5-6 mm |
| Diameter of unthreaded shank 18 | 2.9-3 mm |
| Major diameter of threads 14 | 4-4.5 mm |
| Angle of first tapered transition segment 22 | 4.5 deg. |
| Angle of second tapered transition segment 25 | 15 deg. |

Detailed Method Sequence

Figure 10:
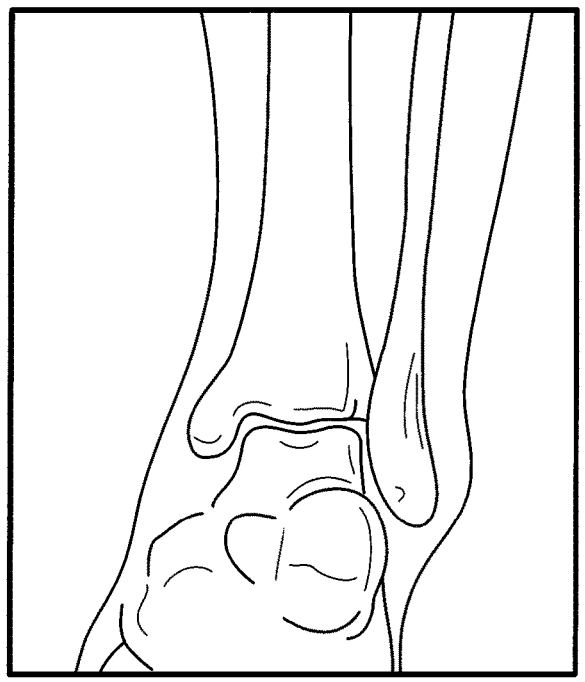
FIGS. 10-12 illustrate lateral, bi-malleolus and tri-malleolus fractures, respectively.
Figure 11:
Figure 12:

As shown in FIGS. 10-12, there are various types of fractures of the malleolus, and the physician will exercise the training and experience to determine the precise manner in which the surgical use of the screw 10 occurs.

Figure 13:
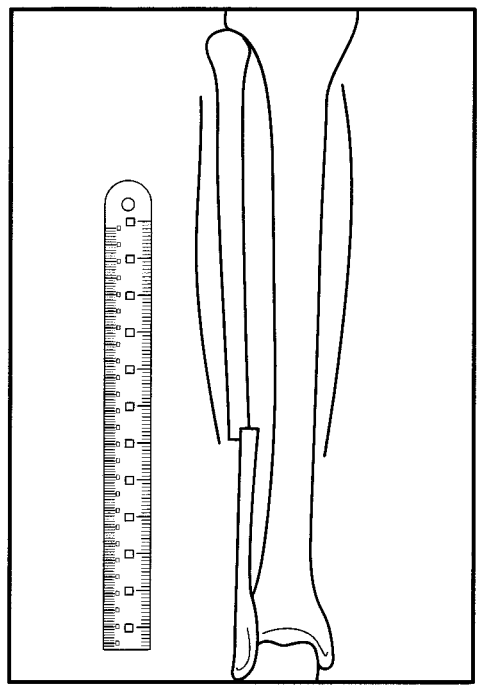

As shown in FIG. 13, a pre-op x-ray is viewed and a ruler is used to determine an estimated length of both proximal and distal portions of the screw 10 to be used. Attention should be taken to the size of the patient's canal. Typically, the 4.0 diameter screw is suitable. Under anesthesia with sterile field, a fluoroscopy unit is used to aid in the surgery. Direct surgeon visualization of the screen is recommended.

Figure 14:
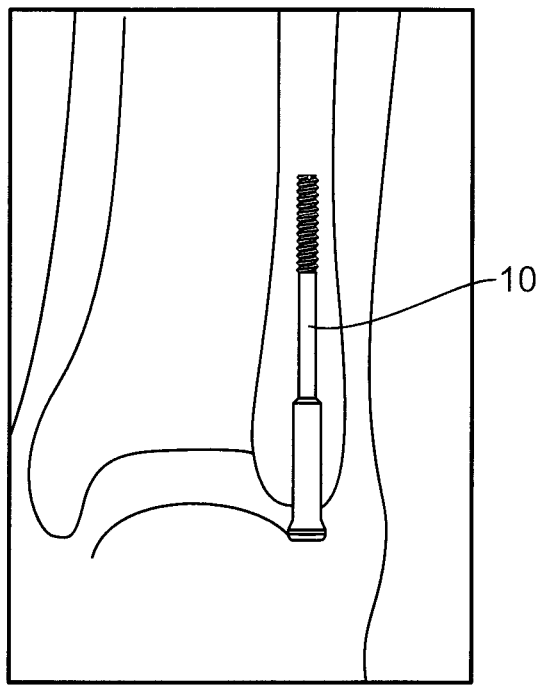

As shown in FIG. 14, (optional), a sterile screw can be placed over the lateral malleolus while taking a fluoroscopic x-ray to determine or verify appropriate screw sizing. Make a small incision as required to expose the distal tip of the fibula.

Figure 15:
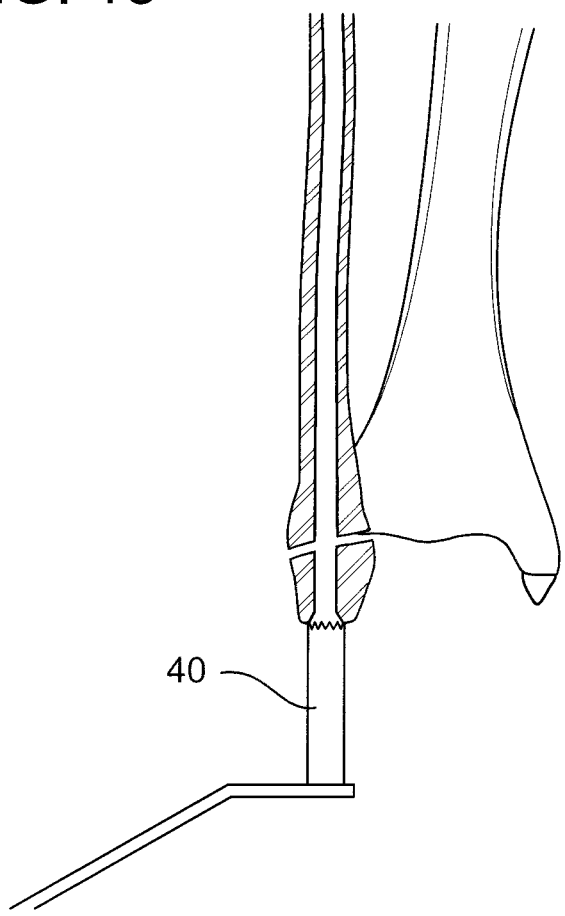

As shown in FIG. 15, with the foot inverted, insert the appropriate sized drill guide 40 until contact is made with the distal fibula. It is required to keep the guide 40 as medial as possible for adequate alignment.

Figure 16:
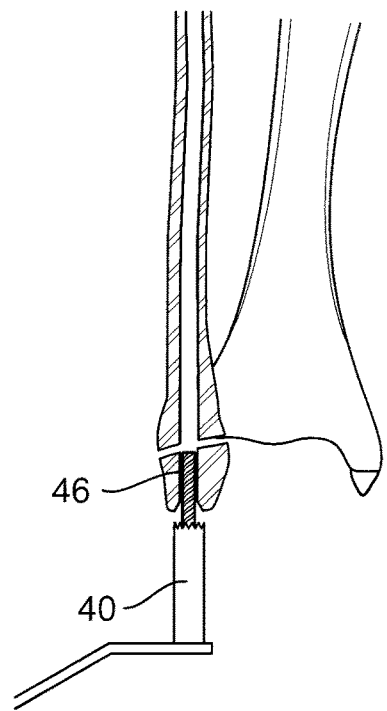

As shown in FIG. 16, insert the appropriate drill bit 46 (4.0 mm or 4.7 mm) through the drill guide 40 creating a small opening in the distal fibula. The drill bit 46 can be inserted up to but not to exceed 40 mm. This depth is determined by the proximal portion of the desired screw 10 to be used. Under drilling may help create added compression during screw insertion. If drilling to the full depth of the proximal measurement of the screw 10, this depth can be read off of the laser marking on the drill bit 46, see FIG. 18.

Figure 17:
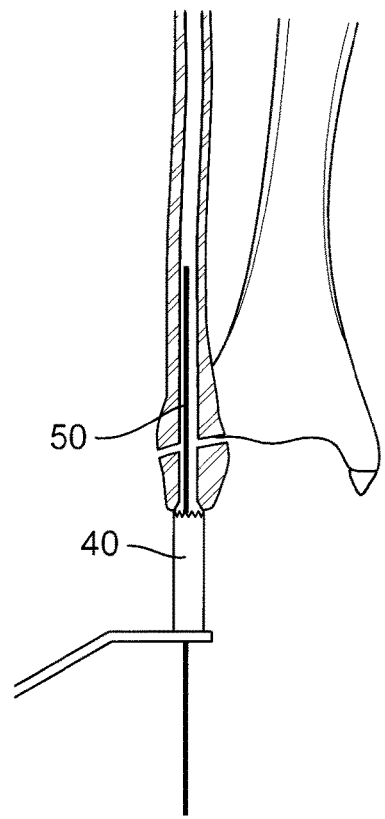

As shown in FIG. 17, remove the drill bit 46 and insert a 225×1.3 mm k-wire 50 through the drill guide 40 and up the fibular canal using low power. Utilization of anterior/posterior and lateral fluoroscopy is required as the k-wire 50 is advanced up the canal of the fibula. Depth of the k-wire 50 should be inserted to a depth at least 25 mm past the fracture to create adequate compression. Optionally, the drill bit 46 may be left in the canal at this point as an aid to direct the k-wire 50 up the canal. Using this method will require use of the 300×1.3 mm k-wire 50.

Figure 18:
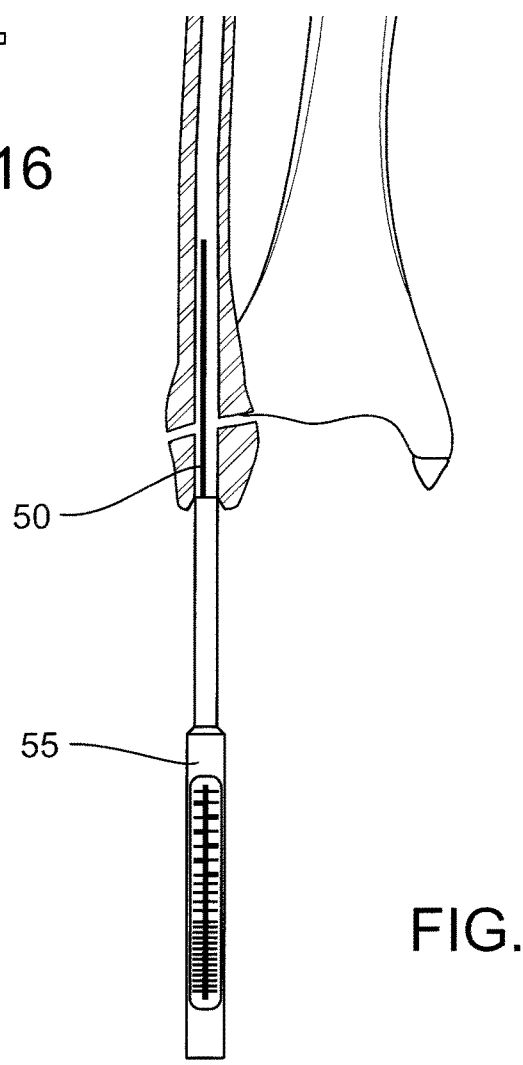

As shown in FIG. 18, remove the drill guide 50 and drill bit 46. Use a wire depth gauge 55 to gauge the total length of the screw 10 to be used. If there is some displacement at the fracture site, it can be reduced before the k-wire 50 insertion with a bone clamp through the skin of a small incision. Remove the wire depth gauge 55 and choose the appropriate screw 10 diameter based on prior measurements and preoperative planning.

Figure 19:
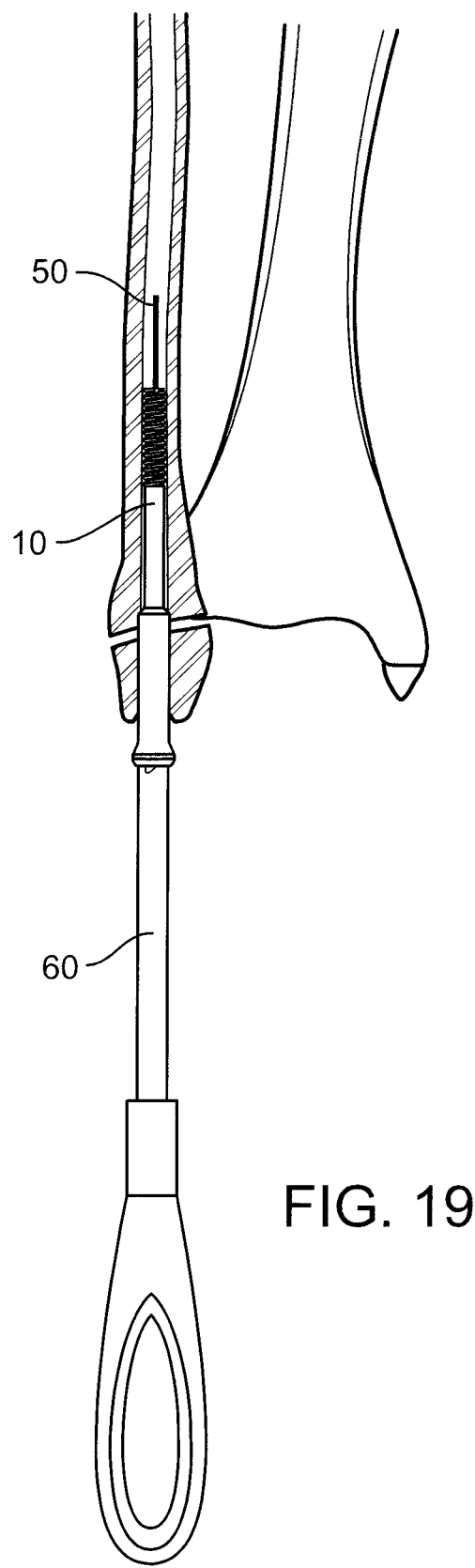

As shown in FIG. 19, insert the screw 10 over the k-wire 50 by hand with a screwdriver 60. Hand insertion helps gauge the feel and adequate purchase of the threads. Fluoroscopy should be used to verify placement of the screw 10 above the fracture site. Continue until the head of the screw 10 is countersunk into the distal fibula. In dense bone, it may be required to use the countersink reamer on the screw driver 60 prior to screw insertion.

Figure 20:
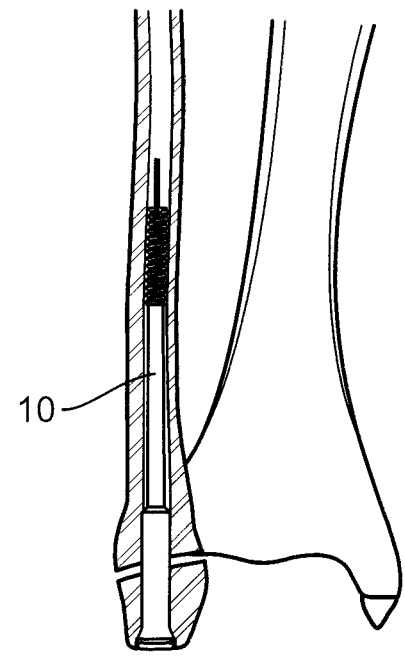

As shown in FIG. 20, confirm by anterior/posterior and lateral fluoroscopy the correct placement of the screw 10. Remove the k-wire 50 and close the incision as desired by clip, suture, or steri-strips. Post op immobilization is at the discretion of the surgeon.

Alternative Detailed Method Sequence

This advanced surgical technique can be used by discretion of the surgeon and per the patient's needs.

Figure 21:
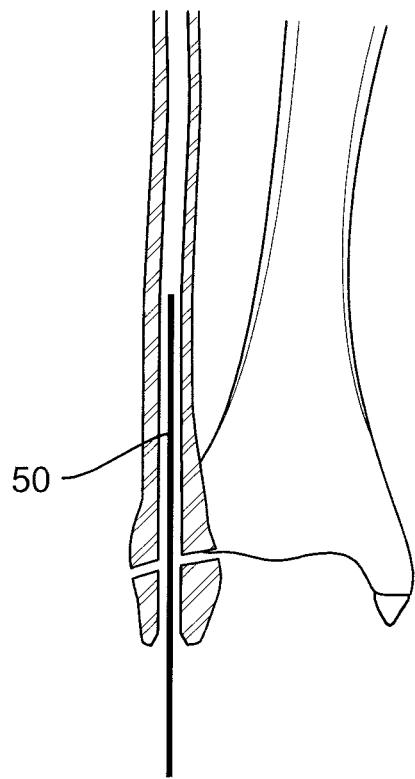

As shown in FIG. 21, insert a 225×1.3 mm k-wire 50 by pressure into the canal to the desired depth. The drill guide 40 may be used as desired as a tissue protector.

Figure 22:
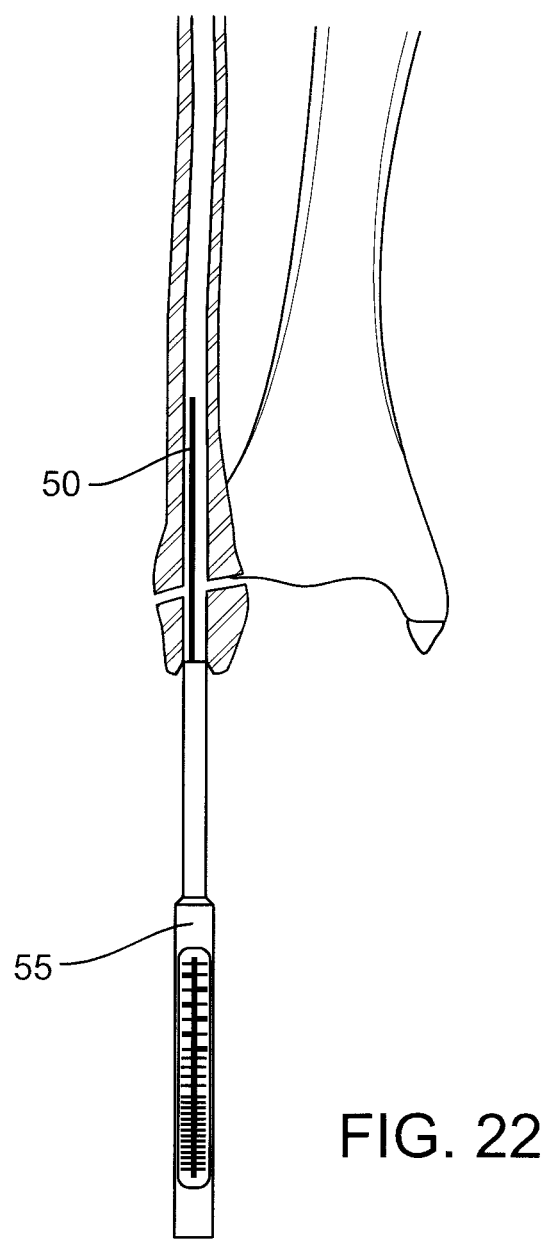

As shown in FIG. 22, place the wire depth gauge 55 over the k-wire 50 until the gauge 55 contacts the distal fibula. Overall screw length is read off the end of the k-wire 50.

Figure 23:
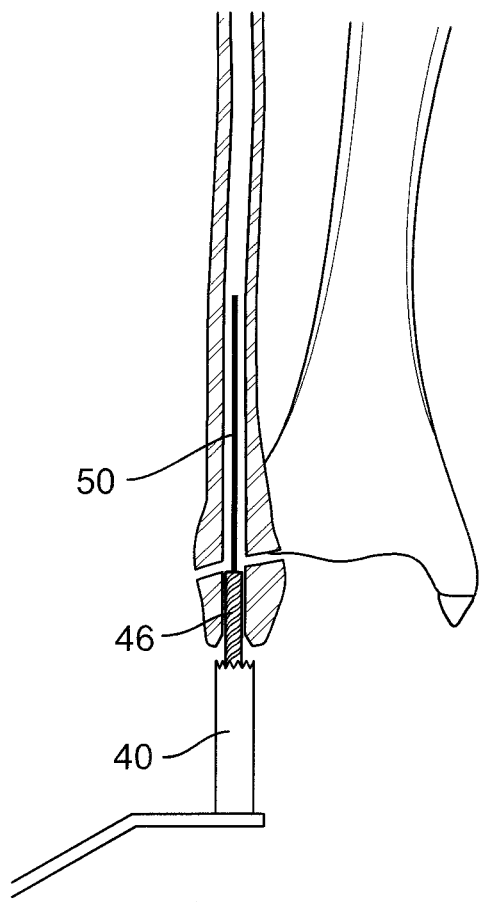

As shown in FIG. 23, remove the wire depth gauge 55 and drill the distal fibula over the k-wire 50 with the appropriate sized drill bit 46 to the desired depth of the proximal screw portion.

Figure 24:
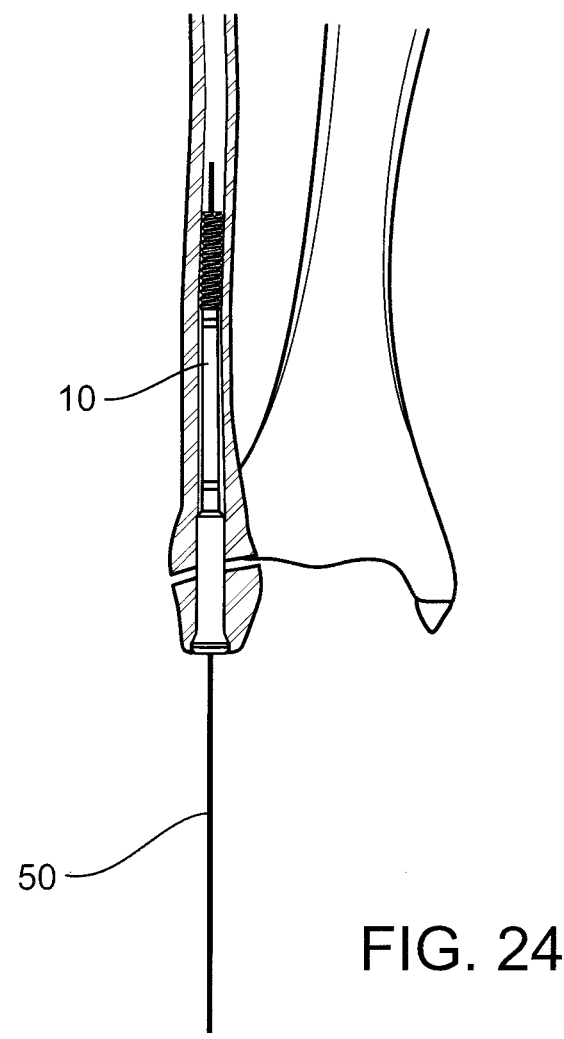

As shown in FIG. 24, advance the appropriate sized screw 10 up the canal over the k-wire 50 with the screwdriver, removing the k-wire 50 after insertion.

Figure 25:
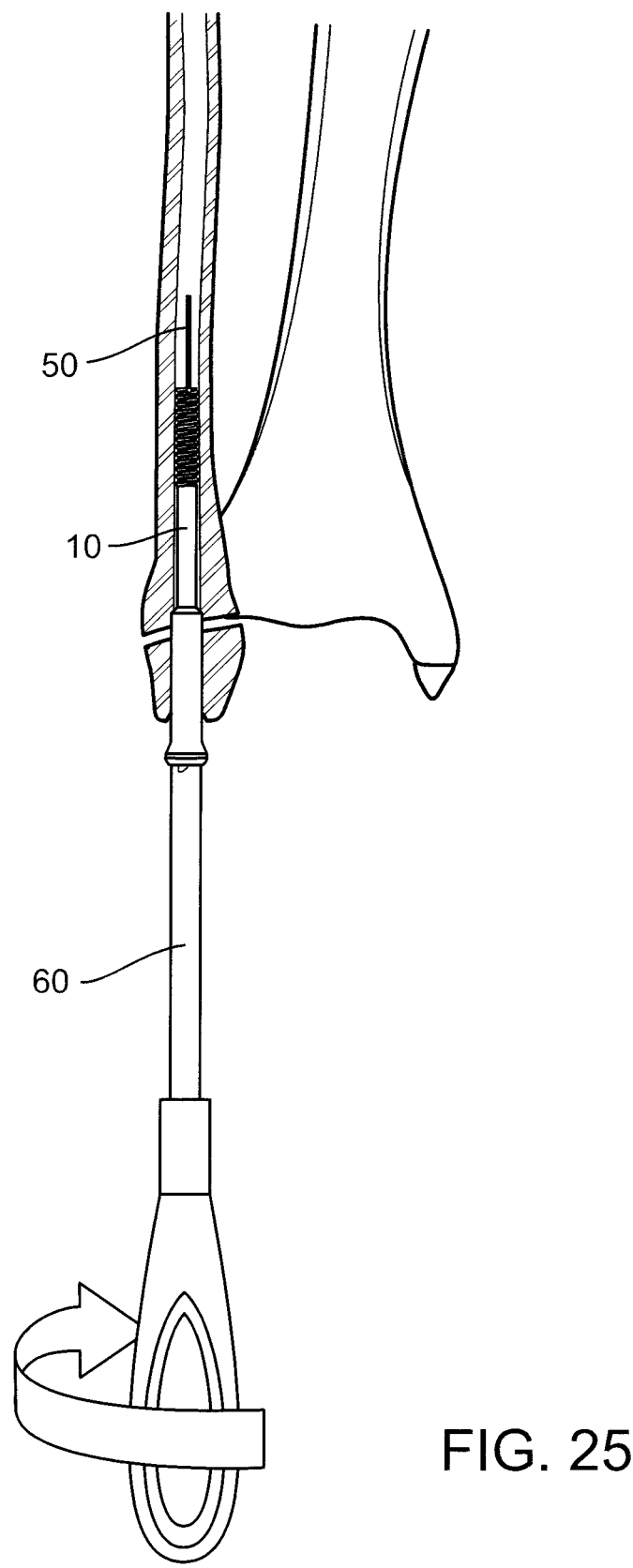

As shown in FIG. 25, should the screw need to be removed, under anesthesia make a small incision in the skin below the fibula. Insert a k-wire 50 through the screw 10 and use the screwdriver 60 to remove the screw 10 and close the incision. However, for some patients, the screw 10 may not easily withdraw due to the screw threads stripping the fibular canal. In some implementations, this may result in the screw 10 rotating within the fibular canal without easily being removed. Alternatively or additionally, in some instances, calcification or various other buildup (ongrowth of new bone—osseoincorporation) may occur near the head 20 of the screw 10, which can impede removal without a way to securely affix the screwdriver 60 to the screw 10 in order to remove the screw. In other examples, the head 20 of the screw 10 may itself become stripped, which can also lead to difficulty removing the screw 10.

Numerous solutions may exist for addressing some of these issues. One existing process to remove implants that are not easily removed may include using pliers used to grip the head 20 of the screw 10; however, this may not work well if there is buildup around the head 20 of the screw 10. Further, depending upon how well inserted the screw 10 is in the fibula, there may not be a lip or other outcropping on the head to grip with the pliers. Some existing methods have proposed using temperature change (e.g. endo ice used in a dental setting) to freeze or chill the metal of the implant thereby slightly shrinking the screw 10 so that it could be more easily removed. However, this technique risks damaging surrounding tissue and may not sufficiently shrink the screw 10. If the head threading is stripped, one existing technique used to resolve this issue is to use glue to fill the head threading and to wait until it dries in order to provide better grip to the screwdriver, but this can be a prolonged process during surgery and would not be in the best interest of the patient. Another approach has been to increase friction using an abrasive that is positioned between the screwdriver and the threads of the head 20, but this may cause abrasion to other tissues.

Thus, the prior art has various shortcomings, and a need exists for improved methods, devices, and kits that can more easily facilitate removal of an orthopedic screw. Advantageously, disclosed herein is an orthopedic screw that includes, in part, a threaded cannula portion centrally located within a socket of an enlarged terminal end segment of a head of the orthopedic screw and at a focus point of the enlarged terminal end, where the threaded cannula portion extends along a cannula for at least a portion of a length of the head. Further, the threaded cannula portion includes a second threaded alignment opposite the first threaded alignment of the screw threads and configured to receive an instrument head adapted for rotating the implanted orthopedic screw for removal. The threaded cannula portion provides the physician with a way to insert an instrument head into the threaded cannula portion and affix the instrument head to the orthopedic screw such that the orthopedic screw can be more easily removed, particularly if the fibular canal is stripped or build up has occurred near the head of the orthopedic screw.

Figure 26A:
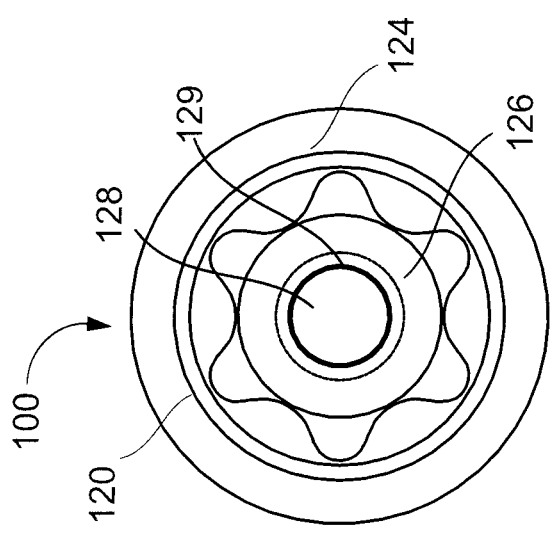
FIG. 26A illustrates a perspective view of the head of an implant, according to one embodiment.

FIG. 26A illustrates a perspective view of the head 120 of an implant 100, according to one embodiment. The head 120 includes an enlarged proximal end 124 that includes a socket 126 for receiving a tool (e.g. a screwdriver with a hex or a star tool head) adapted for rotating the implant/screw 100 into one or more bone segments at the fracture site. Further, as shown, a threaded cannula portion 129 of a cannula 128 is centrally located at a focus point of the enlarged terminal end 124. The threaded cannula portion 129 comprises a hollow cylindrical channel that forms a portion of the cannula 128.

Figure 26B:
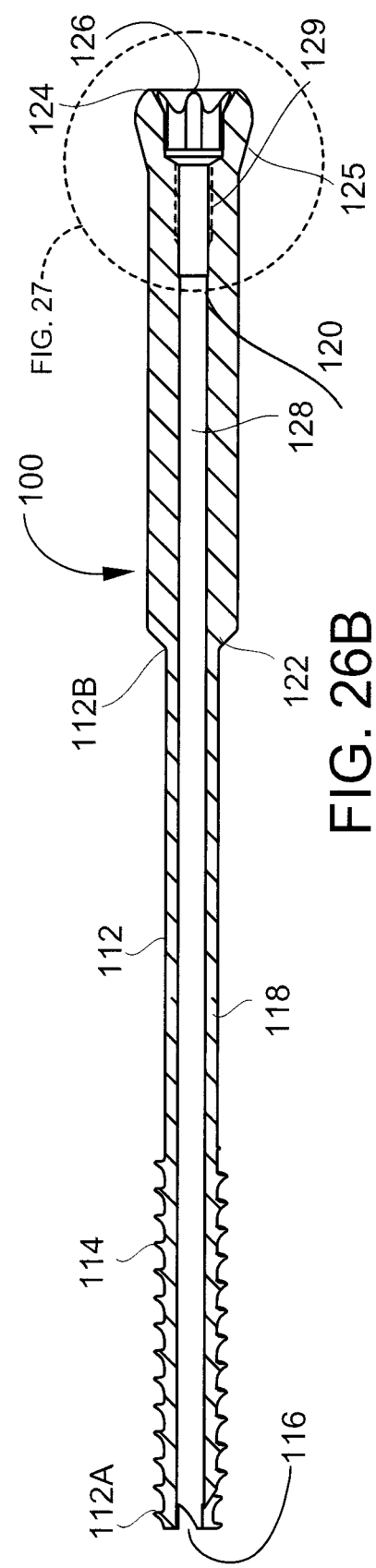
FIG. 26B illustrates a cross-sectional view of the implant of FIG. 26A.
Figure 26C:
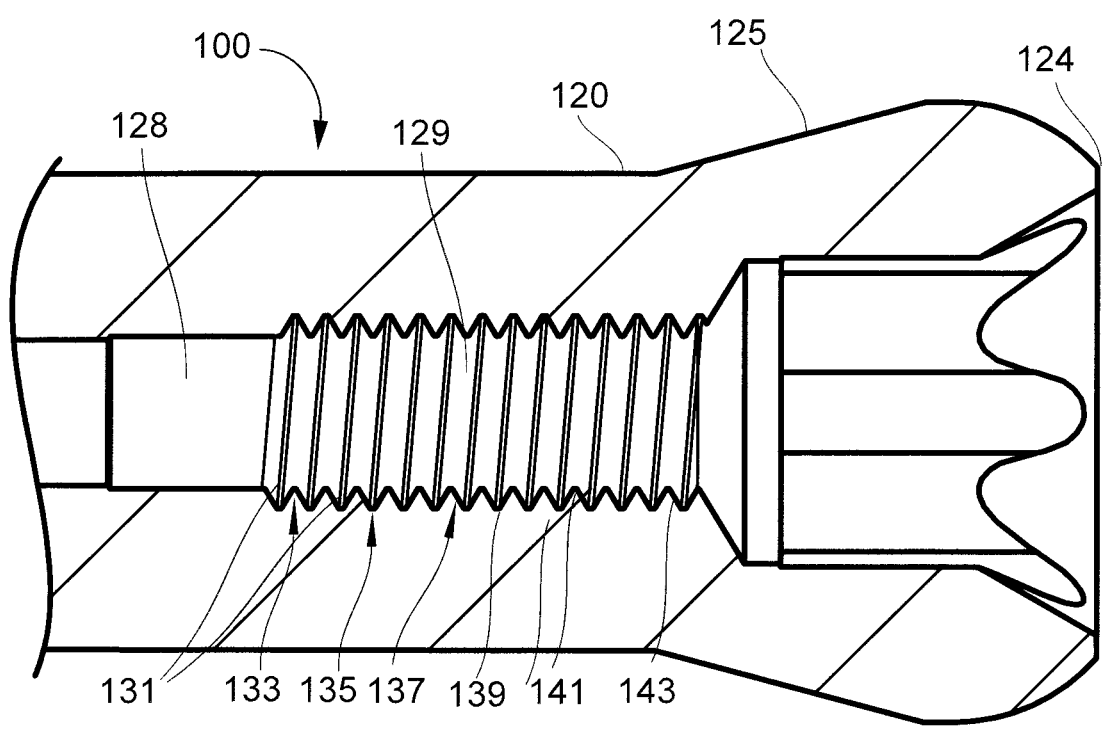
FIG. 26C illustrates a magnified view of a portion of the cross-section of the implant of FIG. 26B.

FIG. 26B illustrates a cross-sectional view of the implant 100 of FIG. 26A, and FIG. 26C depicts a magnified view of the portion of the cross-section of the implant 100. The head 120 includes a length extending from an enlarged proximal end 124 and the second end 112B of the shaft 112. As depicted, the threaded cannula portion 129 extends along the cannula 128 for at least a portion of the length of the head 120. Further, the implant 100 includes a unitary shaft 112 with screw threads 114 with a first threaded alignment formed on the shaft 112 proximate a distal first end 112A of the shaft 112. The screw threads 114 terminate at a sharp, biting end edge 116 adapted to facilitate passage of the implant/screw 100 through one or more bone segments. Further, the threaded cannula portion 129 includes a threaded alignment that is opposite the first threaded alignment of the screw threads 114. Further, the threaded cannula portion 129 is configured to receive an instrument head (e.g. see FIGS. 27-29) adapted for rotating the implant/screw 100 for removal.

An unthreaded shank 118 of the shaft 112 extends to a proximate second end 112B of the shaft 112 and has a diameter less than the major diameter of the screw threads 114. A head 120 is formed on the second end 112B of the shaft 112 with a first tapered transition segment 122 formed at the juncture of the shaft 112 and an elongate enlarged head 120 such that rotation of the implant/screw 100 provides progressively increased fracture-reducing pressure between the one or more bone segments as described above. The head 120 transitions to the proximal end 124 of the head 120 by a second tapered transition segment 125 positioned at a juncture of the head 120 and the enlarged terminal end segment of the head 120. The second tapered transition segment 125 helps provide progressively increased fracture-reducing pressure to the one or more bone segments. The head 120 has a predetermined large diameter in relation to the diameter of the shaft 112. Further, the threaded cannula portion 129 includes a diameter (i.e., a major diameter) that is less than a total diameter of the socket 126. The threaded cannula portion 129 includes threads 131 having a root 133 and a crest 135 and include a thread angle 137 sized and shaped or otherwise configured to align with threads 254 (see FIG. 27) of a threaded end 252A (see FIG. 27) of an instrument 200 (see FIG. 27) for implant removal. The threads 131 include multiple diameters, where the major diameter 139 (corresponding to the crest 135) is less than a total diameter of the socket 126 and is the widest point of the threads 131, a minor diameter 141 (corresponding to the root 133) is the narrowest point of the threads, and a pitch diameter 143 varies across the thread angle 137 of the threads 131.

FIG. 27 illustrates a perspective view of a kit that includes the implant 100 of FIGS. 26A-26C and an instrument 200 for implant removal, according to one embodiment. The instrument 200 includes an instrument head 250 and includes an instrument shaft 252 extending from a threaded end 252A to a tang end 252B, wherein threads 254 of the threaded end 252A are configured to correspond to threads 131 (see FIGS. 26A-26C) of the threaded cannula portion 129. Further, a tang 256 of the tang end 252B include a notched head 258 configured to fit into a driving device socket of a driving device (e.g. a socket wrench screwdriver). According to one embodiment, the notched head 258 includes a partially cylindrical configuration. For example, in some embodiments, a portion of the notched head may be shaved, cut, or otherwise missing from the cylindrical configuration such that the notched head may only be partially cylindrical.

FIG. 28A illustrates a cross sectional view and FIG. 28B illustrates a perspective view of the implant 100 of FIGS. 26A-27 with the instrument 200 for implant removal of FIG. 27 inserted therein, according to one embodiment. The threaded end 252A of the instrument 200 is secured to the implant 100 via the threaded cannula portion 129 of a cannula 128 that is located at the focus point of the enlarged terminal end 124 of the implant 100.

Figure 29:
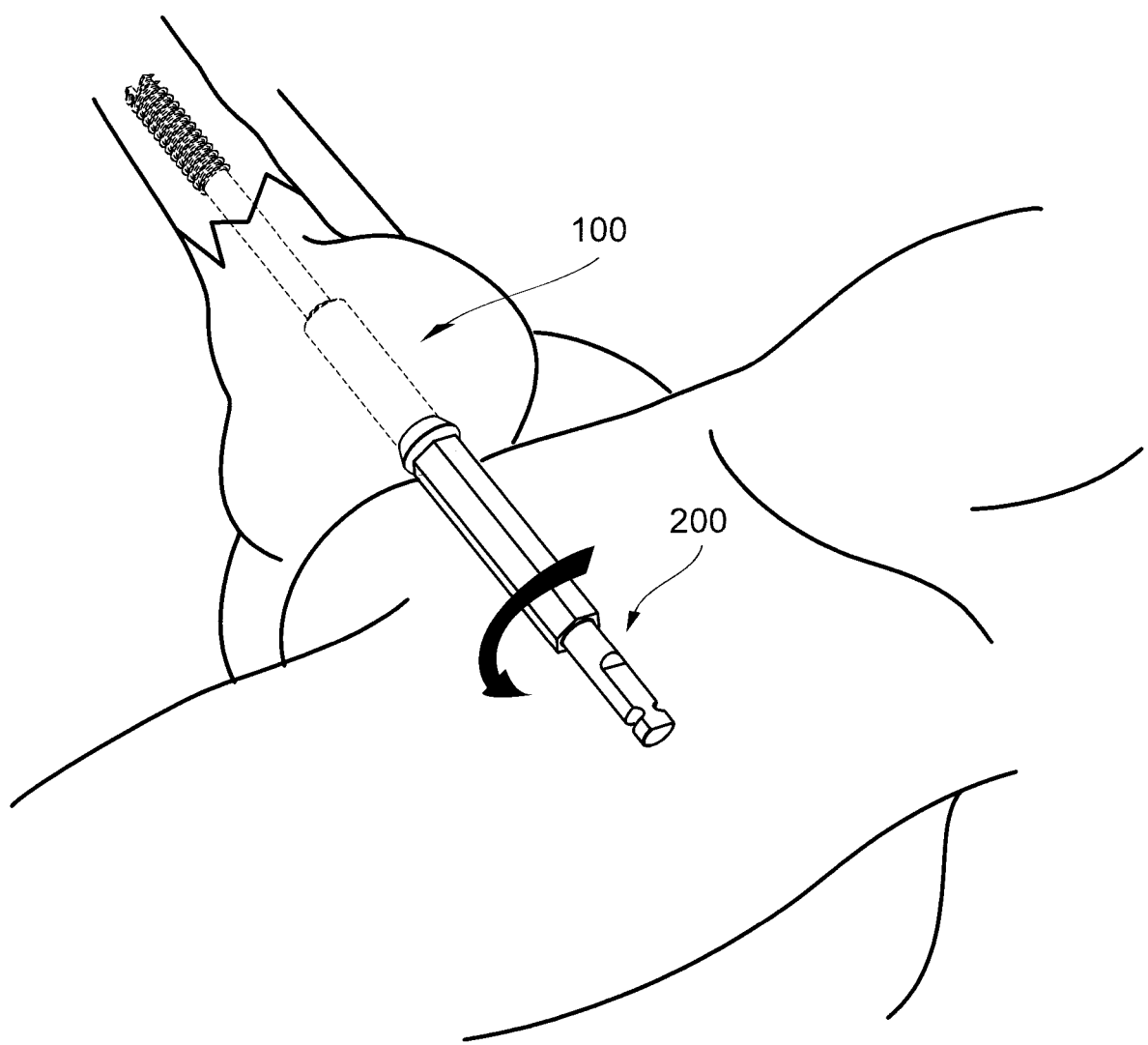
FIG. 29 illustrates a method of implant removal, according to one embodiment.

FIG. 29 illustrates a method of implant removal, according to one embodiment. As depicted the instrument 200 is affixed to the implant 100 by turning the instrument 200 counter clockwise. Once secured, the physician would then continue to turn the instrument 200 to the left in order to dislodge the implant 100 from the one or more bone segments.

FIG. 30 illustrates example method 300 steps for removing an implant, according to one embodiment. At block 305, a physician would access an implanted orthopedic screw previously implanted in one or more bone segments of a patient, where the orthopedic screw includes a unitary shaft and includes (i) screw threads that include a first threaded alignment, that have a diameter, and that are formed on a first, distal end of the shaft. Further, a terminal end portion of the screw threads includes an end edge adapted to facilitate passage of the screw through the one or more bone segments at a fracture site. The orthopedic screw also includes (ii) an unthreaded shank having a diameter less than the diameter of the screw threads, and (iii) a head positioned on a second, proximal end of the shaft integrally-formed to the shank and having a diameter greater than the diameter of the screw threads and the shank. The orthopedic screw also includes (iv) an enlarged terminal end segment of the head that includes (1) a socket for receiving a tool adapted for rotating the screw into the one or more bone segments at the fracture site, and (2) a threaded cannula portion centrally located within the socket at a focus point of the enlarged terminal and extending along a cannula for at least a portion of a length of the head. The threaded cannula portion includes a second threaded alignment opposite the first threaded alignment of the screw threads and is configured to receive an instrument head adapted for rotating the implanted orthopedic screw for removal.

At block 310, the instrument head adapted for rotating the implanted orthopedic screw is fastened to the threaded cannula portion of the enlarged terminal end. At block 315, the implanted orthopedic screw is at least partially withdrawn from the one or more bone segments by rotating the instrument head.

In some embodiments, the method 300 further includes making an incision to the patient's skin across the patient's lateral malleolus and centered along a long axis of the patient's fibular shaft and retracting the skin to access the implanted orthopedic screw. Further, the method 300 may also include closing the incision.

Aspects of the present invention are described herein with reference to flowchart illustrations and/or block diagrams according to embodiments of the invention. It will be understood that each block of the flowchart illustrations and/or block diagrams, and combinations of blocks in the flowchart illustrations and/or block diagrams, can be performed out of the order noted in the Figures. For example, two blocks shown in succession may, in fact, be executed substantially concurrently, or the blocks may sometimes be executed in the reverse order, depending upon the process involved.

While the invention has been described in relation to medical treatment of humans and specifically the reduction of a fracture of the lateral malleolus and fibula, the screw according to the disclosure of this application has applications in fracture reduction in other parts of the human body and in veterinary medical practice.

A cannulated orthopedic screw according to the invention has been described with reference to specific embodiments and examples. Various details of the invention may be changed without departing from the scope of the invention. Furthermore, the foregoing description of the preferred embodiments of the invention and best mode for practicing the invention are provided for the purpose of illustration only and not for the purpose of limitation, the invention being defined by the claims.

I claim:

1. A surgical method, comprising the steps of:
   (a) accessing an implanted orthopedic screw previously implanted in one or more bone segments of a patient, the orthopedic screw, comprising a unitary shaft, including:
      (i) screw threads comprising a first threaded alignment and having a diameter and formed on a first, distal end of the shaft, a terminal end portion of the screw threads including an end edge adapted to facilitate passage of the screw through the one or more bone segments at a fracture site;
      (ii) an unthreaded shank having a diameter less than the diameter of the screw threads;
      (iii) a head positioned on a second, proximal end of the shaft integrally-formed to the shank and having a diameter greater than the diameter of the screw threads and the shank;
      (iv) an enlarged terminal end segment of the head including:
         (1) a socket for receiving a tool adapted for rotating the screw into the one or more bone segments at the fracture site; and
         (2) a threaded cannula portion centrally located within the socket at a focus point of the enlarged terminal end segment and extending along a cannula for at least a portion of a length of the head, the threaded cannula portion comprising a second threaded alignment opposite the first threaded alignment of the screw threads and configured to receive an instrument head adapted for rotating the implanted orthopedic screw for removal; and
   (b) fastening the instrument head adapted for rotating the implanted orthopedic screw to the threaded cannula portion of the enlarged terminal end segment, wherein the instrument head comprises an instrument shaft extending from a threaded end to a tang end, wherein threads of the threaded end are configured to correspond to threads of the threaded cannula portion, and wherein a tang of the tang end comprises a notched head configured to fit into a driving device socket of a driving device;
   (c) at least partially withdrawing the implanted orthopedic screw from the one or more bone segments by rotating the instrument head.

2. The method according to claim 1, wherein the one or more bone segments comprise lateral malleolus bone fragments, and the method further comprises the steps of:
   (d) making an incision to the patient's skin across the patient's lateral malleolus and centered along a long axis of the patient's fibular shaft; and
   (e) retracting the skin to access the implanted orthopedic screw.

3. The method according to claim 2, wherein method further comprises the steps of:
   (f) closing the incision.

4. The method according to claim 1, wherein the orthopedic screw further comprises:
   (v) a first tapered transition segment formed at a juncture of the shaft and head such that rotation of the screw during implantation provides progressively increased fracture-reducing pressure to the one or more bone segments; and
   (vi) a second tapered transition segment formed at a juncture of the head and the enlarged terminal end segment of the head such that rotation of the screw during implantation provides progressively increased fracture-reducing pressure to the one or more bone segments.

5. The method according to claim 1, step (c) further comprises fully removing the implanted orthopedic screw.

6. The method according to claim 1, wherein the threaded cannula portion comprises a hollow cylindrical channel.

7. The method according to claim 1, wherein the threaded cannula portion comprises a diameter that is less than a total diameter of the socket.

8. The method according to claim 1, wherein the notched head comprises a partially cylindrical configuration.

9. A surgical kit, comprising:
   (A) an orthopedic screw comprising:
      (i) a unitary shaft extending from a first, distal end to a second, proximal end;
      (ii) screw threads comprising a first threaded alignment and having a diameter and formed on the first, distal end, a terminal end portion of the screw threads including an end edge adapted to facilitate passage of the screw through one or more bone segments at a fracture site;
      (iii) an unthreaded shank having a diameter less than the diameter of the screw threads;
      (iv) a head positioned on the second, proximal end integrally-formed to the shank and having a diameter greater than the diameter of the screw threads and the shank; and
      (v) an enlarged terminal end segment of the head including:
         (1) a socket for receiving a tool adapted for rotating the screw into the one or more bone segments at the fracture site; and
         (2) a threaded cannula portion centrally located at a focus point of the enlarged terminal end segment and extending along a cannula for at least a portion of a length of the head, the threaded cannula portion comprising a second threaded alignment opposite the first threaded alignment of the screw threads and configured to receive an instrument head; and
   (B) the instrument head adapted for rotating the implanted orthopedic screw for removal and comprising an instrument shaft extending from a threaded end to a tang end, wherein threads of the threaded end are configured to correspond to threads of the threaded cannula portion, and wherein a tang of the tang end comprises a notched head configured to fit into a driving device socket of a driving device.

10. The surgical kit of claim 9, wherein the orthopedic screw further comprises:
    (vi) a first tapered transition segment formed at a juncture of the shaft and head such that rotation of the screw provides progressively increased fracture-reducing pressure to the one or more bone segments; and
    (vii) a second tapered transition segment formed at a juncture of the head and the enlarged terminal end segment of the head such that rotation of the screw provides progressively increased fracture-reducing pressure to the one or more bone segments.

11. The surgical kit of claim 9, wherein the threaded cannula portion comprises a hollow cylindrical channel.

12. The surgical kit of claim 9, wherein the threaded cannula portion comprises a diameter that is less than a total diameter of the socket.

13. The surgical kit of claim 9, wherein the notched head comprises a partially cylindrical configuration.

14. The surgical kit of claim 9, further comprising (C) a driving device.

* * * * *